United States Patent
Ikuta et al.

(10) Patent No.: US 10,321,810 B2
(45) Date of Patent: Jun. 18, 2019

(54) SPECTRALLY ENCODED ENDOSCOPIC PROBE HAVING A FIXED FIBER

(71) Applicants: Canon U.S.A., Inc., Melville, NY (US); The General Hospital Corporation, Boston, MA (US)

(72) Inventors: Mitsuhiro Ikuta, Cambridge, MA (US); Dukho Do, Malden, MA (US); DongKyun Kang, Somerville, MA (US); Guillermo J. Tearney, Cambridge, MA (US); Jacob Schieffelin Brauer, Cambridge, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 436 days.

(21) Appl. No.: 15/180,722

(22) Filed: Jun. 13, 2016

(65) Prior Publication Data

US 2017/0354317 A1 Dec. 14, 2017

(51) Int. Cl.
*G01J 3/00* (2006.01)
*A61B 1/00* (2006.01)
*A61B 1/06* (2006.01)
*A61B 1/07* (2006.01)
*G01J 3/10* (2006.01)
(Continued)

(52) U.S. Cl.
CPC ........ *A61B 1/0017* (2013.01); *A61B 1/00096* (2013.01); *A61B 1/00172* (2013.01); *A61B 1/00188* (2013.01); *A61B 1/06* (2013.01); *A61B 1/07* (2013.01); *A61B 5/0075* (2013.01); *G01J 3/0218* (2013.01); *G01J 3/10* (2013.01); *G01J 3/18* (2013.01); *G02B 23/2423* (2013.01); *G02B 23/26* (2013.01); *A61B 5/6852* (2013.01)

(58) Field of Classification Search
CPC ........ G01J 3/28; G01J 3/44; G01J 3/02; G01J 3/00; G01J 3/10; G01J 3/18; G01J 3/12; G01J 3/45; G02B 5/18; G01B 9/02
See application file for complete search history.

(56) References Cited

U.S. PATENT DOCUMENTS 3,976,360 A    8/1976  Schroder
4,074,306 A    2/1978  Kakinuma et al.
(Continued)

FOREIGN PATENT DOCUMENTS

CN    204207708 U    3/2015
WO    2007/084903 A1    7/2007
(Continued)

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.
(Continued)

*Primary Examiner* — Abdullahi Nur
(74) *Attorney, Agent, or Firm* — Canon U.S.A., Inc., IP Division (57) ABSTRACT

Exemplary apparatus, systems, methods of making, and methods of using a configuration in an optical arrangement for spectrally encoded endoscopy (SEE) probe can be provided. For example, the probe can comprise a fixed guiding portion and a rotatable dispersive portion.

23 Claims, 6 Drawing Sheets

(51) Int. Cl.
*G01J 3/18* (2006.01)
*G02B 23/24* (2006.01)
*G02B 23/26* (2006.01)
*G01J 3/02* (2006.01)
*A61B 5/00* (2006.01)

(56) References Cited

U.S. PATENT DOCUMENTS

| | | |
|---|---|---|
| 4,264,127 A | 4/1981 | Schumacher et al. |
| 5,279,280 A | 1/1994 | Bacich et al. |
| 5,565,983 A | 10/1996 | Barnard |
| 5,909,529 A | 6/1999 | Bhagavatula |
| 5,921,926 A | 7/1999 | Rolland et al. |
| 6,341,036 B1 | 1/2002 | Tearney et al. |
| 6,445,198 B1 | 9/2002 | Akikuni et al. |
| 6,485,413 B1 | 11/2002 | Boppart et al. |
| 6,661,513 B1 | 12/2003 | Granger |
| 6,831,781 B2 | 12/2004 | Tearney et al. |
| 6,858,859 B2 | 2/2005 | Kusunose |
| 7,003,196 B2 | 2/2006 | Ghiron |
| 7,342,659 B2 | 3/2008 | Horn et al. |
| 7,448,995 B2 | 11/2008 | Wiklof et al. |
| 7,796,270 B2 | 9/2010 | Yelin et al. |
| 7,843,572 B2 | 11/2010 | Tearney et al. |
| 7,859,679 B2 | 12/2010 | Bouma et al. |
| 8,045,177 B2 | 10/2011 | Tearney et al. |
| 8,145,018 B2 | 3/2012 | Shishkov et al. |
| 8,203,708 B2 | 6/2012 | Lee et al. |
| 8,289,522 B2 | 10/2012 | Tearney et al. |
| 8,323,183 B2 | 12/2012 | Feldman et al. |
| 8,780,176 B2 | 7/2014 | Yelin |
| 8,792,757 B2 | 7/2014 | Boudoux et al. |
| 8,804,133 B2 | 8/2014 | Yelin et al. |
| 8,812,087 B2 | 8/2014 | Yelin et al. |
| 8,818,149 B2 | 8/2014 | Shishkov et al. |
| 8,838,213 B2 | 9/2014 | Tearney et al. |
| 9,046,419 B2 | 6/2015 | Yelin et al. |
| 9,057,594 B2 | 6/2015 | Kang et al. |
| 9,254,089 B2 | 2/2016 | Tearney et al. |
| 2002/0114566 A1 | 8/2002 | Fairchild et al. |
| 2002/0145815 A1 | 10/2002 | Moriyama et al. |
| 2003/0027328 A1 | 2/2003 | Cunningham et al. |
| 2003/0142934 A1 | 7/2003 | Pan et al. |
| 2004/0147810 A1 | 7/2004 | Mizuno |
| 2004/0174529 A1 | 9/2004 | Maznev et al. |
| 2005/0155704 A1 | 7/2005 | Yokajty et al. |
| 2007/0188855 A1 | 8/2007 | Shishkov et al. |
| 2007/0233396 A1 | 10/2007 | Tearney et al. |
| 2007/0276187 A1 | 11/2007 | Wiklof et al. |
| 2008/0013960 A1 | 1/2008 | Tearney et al. |
| 2008/0097225 A1 | 4/2008 | Tearney et al. |
| 2009/0141360 A1 | 6/2009 | Koyama |
| 2009/0153932 A1 | 6/2009 | Davis et al. |
| 2010/0210937 A1 | 8/2010 | Tearney et al. |
| 2011/0237892 A1 | 9/2011 | Tearney et al. |
| 2011/0275899 A1 | 11/2011 | Tearney et al. |
| 2011/0282166 A1* | 11/2011 | Chen .................... A61B 5/0084 600/306 |
| 2012/0112094 A1 | 5/2012 | Kao et al. |
| 2012/0212595 A1 | 8/2012 | Parmar et al. |
| 2013/0012771 A1 | 1/2013 | Robertson |
| 2013/0331709 A1 | 12/2013 | Le et al. |
| 2014/0153864 A1 | 6/2014 | Sinclair et al. |
| 2014/0221747 A1 | 8/2014 | Tearney et al. |
| 2014/0285878 A1 | 9/2014 | Escuti et al. |
| 2014/0378846 A1 | 12/2014 | Hosoda et al. |
| 2015/0045622 A1 | 2/2015 | Shishkov et al. |
| 2015/0131098 A1 | 5/2015 | Yang et al. |
| 2015/0231841 A1 | 8/2015 | Tearney et al. |
| 2015/0335248 A1 | 11/2015 | Huang et al. |
| 2017/0176736 A1 | 6/2017 | Yamamoto et al. |

FOREIGN PATENT DOCUMENTS

| | | |
|---|---|---|
| WO | 2014031748 A1 | 2/2014 |
| WO | 2014104405 A1 | 7/2014 |
| WO | 2015/042093 A1 | 3/2015 |
| WO | 2015116939 A1 | 8/2015 |
| WO | 2015116951 A1 | 8/2015 |
| WO | 2015116951 A2 | 8/2015 |
| WO | 2015116974 A1 | 8/2015 |
| WO | 2017/024145 A1 | 2/2017 |
| WO | 2017/106347 A1 | 6/2017 |
| WO | 2017/117203 A1 | 7/2017 |
| WO | 2017/139657 A1 | 8/2017 |

OTHER PUBLICATIONS

Pitris, C. et al. "A GRISM-based probe for spectrally encoded confocal microscopy" Optics Express, Jan. 27, 2003, pp. 120-124, vol. 11, No. 2.

Yelin, D., et al., "Three-dimensional miniature endoscopy", Nature, Oct. 19, 2006, p. 765, vol. 443.

Kang, D., et al., "Minature grating for spectrally-encoded endoscopy", Lab Chip, 2013, pp. 1810-1816, vol. 13.

Kang, D., et al., "Spectrally-encoded color imaging", Optics Express, Aug. 17, 2009, pp. 15239-15247, vol. 17, No. 17.

Yun, et al., "High-speed spectral-domain optical coherence tomography at 1.3 µm wavelength", Opt Express, Dec. 29, 2003, pp. 3598-3604, No. 11, vol. 26.

Zeidan, A., et al., "Miniature forward-viewing spectrally encoded endoscopic probe", Optics Letters, Aug. 15, 2014, pp. 4871-4784, vol. 39, No. 16.

Yelin, D., et al., "Three-dimensional miniature endoscopy", Nature, Oct. 19, 2006, vol. 443.

Kang, D., et al. "Miniature grating for spectrally-encoded endoscopy," Lab on a Chip, 2013, pp. 1810-1816, vol. 13.

Tearney, G.J., et al., "Spectrally encoded miniature endoscopy", Optics Letters, Mar. 15, 2002, pp. 412-414, vol. 27, No. 6.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

Barlev, O., et al., "Design and experimental investigation of highly efficient resonance-domain diffraction gratings in the visible spectral region", Applied Optics, Dec. 1, 2012, pp. 8074-8080, vol. 51, No. 34.

\* cited by examiner

SPECTRALLY ENCODED ENDOSCOPIC PROBE HAVING A FIXED FIBER

FIELD OF THE DISCLOSURE

The present disclosure relates generally to exemplary apparatus and method for endoscopy and, more particularly to exemplary spectrally encoded endoscopy probes.

BACKGROUND INFORMATION

Medical probes have the ability to provide images from inside the patient's body. Considering the potential damage to a human body caused by the insertion of a foreign object, it is preferable for the probe to be as small as possible. Additionally, the ability to image within small pathways such as small vessels, small ducts, small needles, cracks etc., requires a small probe size.

One useful medical probe employs a spectrally encoded endoscopy ("SEE"), which is a miniature endoscopy technology that can conduct high-definition imaging through a mm or sub-mm diameter probe. With SEE, broadband light is diffracted by a grating at the tip of the fiber, producing a dispersed spectrum on the sample. Light returned from the sample is detected using a spectrometer; and each resolvable wavelength corresponds to reflectance from a different point on the sample. In the SEE probe, illumination or/and detection fiber is oscillated or rotated so that illumination/detection area is scanned the rotating spectrally-encoded line.

The principle of the SEE technique and an SEE probe with a diameter of 0.5 mm, i.e., 500 μm have been described in D. Yelin et al., Nature Vol. 443, 765-765 (2006). SEE can produce high-quality images in two- and three-dimensions. SEE probes that image the location in front of the probes have been demonstrated using a 350-μm diameter probe, which produced high-quality images in two- and three-dimensions. See, for example, A Zeidan et al., Optics Letters Vol. 39, Issue 16, pp. 4871-4874 (2014). Zeidan proposes using an optical fiber rotary junction between probe and console (light source or spectrometer) to obtain 360-degree probe rotation.

Similarly, WO 2015/116951 disclosed a forward view SEE, illumination fiber where the fiber and dispersion optics are rotated using a rotary junction. This application is herein incorporated by reference in its entirety. Additional disclosure of SEE probes includes U.S. Pat. No. 8,818,149, which disclosed spectrally encoded endoscopy techniques and apparatus and U.S. Pat. Pub. 2011/0275899, which disclosed a spectrally encoded miniature endoscopic imaging probe. While the rotation of the optical head is discussed for larger probes, for at least narrow vessels, a special rotating junction must be used.

Each of these probes provides a rotary junction for connecting the rotating illumination or detection optics to a non-rotating portion of the fiber. In order to obtain high resolution, it is preferable to use either single-mode fiber (SMF) or small core multi-mode fiber (MMF). Typical core diameters for the MMF is less than 50 μm, for example 5 or 10 μm. Thus, when the probe is connected to a rotary junction in order to allow for rotational motion, the fibers must be carefully coupled to the rotary junction. Light coupling of rotary joint with such fibers is particularly challenging. The coupling efficiency is low, usually less than 50% in the case of SMF-SMF coupling. Additionally, the efficiency fluctuates along the rotation.

Thus, there is need for a new SEE probe and apparatus that does not need the added expense and complication of a rotary junction but allows for scanning of the illumination and/or detection portion

SUMMARY OF EXEMPLARY EMBODIMENTS

According to at least one embodiment of the invention, there is provided a forward viewing probe comprising: a fixed guiding portion and a rotatable dispersive portion.

In some embodiment, the fixed guidance portion comprising: an at least one first light guiding component and an optional first focusing component, wherein the fixed guiding portion is configured to guide a light to a rotatable dispersive portion. The rotatable dispersive portion comprising: an optional second focusing component, wherein at least one of the fixed guiding portion and the rotatable dispersive portion comprises a focusing component; a reflecting component configured to reflect light received from the first or second focusing component onto a dispersing component; and the dispersing component configured to receive light from the reflecting component and forward spectrally-dispersed light thereof, wherein the rotatable dispersive portion is configured to rotate around a probe optical axis, the fixed guiding portion is configured to remain stationary relative to the probe optical axis, and wherein the probe is configured such that at least one wavelength of the spectrally dispersed light propagates from the dispersive component substantially along the probe optical axis.

In some embodiments, the fixed guidance portion comprises: an at least one first light guiding component and a first focusing component, wherein the fixed guiding portion is configured to collimate a light and guide the collimated light to a rotatable dispersive portion, and the rotatable dispersive portion comprising: a second focusing component configured to receive the collimated light; a dispersing component configured to receive the light and forward spectrally-dispersed light thereof, wherein the rotatable dispersive portion is configured to rotate around a probe optical axis, the fixed guiding portion is configured to remain stationary relative to the probe optical axis.

According to at least one embodiment of the invention, there is provided an imaging apparatus comprising: the probe as described above, a broad band light source providing a light to the probe, and a light intensity detector receiving a light from the probe. The imaging apparatus may further comprise a hollow core motor, wherein the rotatable dispersive portion is rotationally attached to a driveshaft of the hollow core motor. The imaging apparatus may further comprise a sheath surrounding both the rotatable dispersive portion and the fixed guiding portion.

The first focusing component of the fixed guiding portion may be, for example, a gradient index (GRIN) lens. The light guiding component may be a single mode optical fiber or a multimode optical fiber (e.g., a MMF having a core diameter of less than 50 μm), and may be optically connected to one of the first light focusing component or the second light focusing component at an off-center position. The light guiding component may provide illumination or both illumination and collection.

The rotatable dispersive portion may, for example, rotate at least 360 degrees or have an oscillating motion. The rotatable dispersive portion may include a spacer component, wherein the reflecting component is located at one surface of the spacer component. The rotatable dispersive portion may also include a second light guiding component configured for collecting light associated with the spectrally dispersed light. In some embodiments for the forward view probe, the dispersing component forwards spectrally dispersed light, where at least one wavelength of the spectrally dispersed light has an angle of less than 5° from the probe optical axis.

According to at least one embodiment of the invention, the probe may also comprise a rotatable prism (e.g., a rotatable dove prism) located between the fixed guiding portion and the rotatable dispersive portion. The rotatable prism may be configured to rotate at approximately half the speed at which the rotatable dispersive portion is configured to rotate.

In some embodiments as provide herein the probe comprises an adjustable space between the fixed guiding portion and the rotatable dispersive portion.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The present invention provides probes, apparatus, and methods for SEE where a rotary junction is not required. Instead of rotating the illumination fiber or other light guiding component, a dispersive portion of the probe is rotated.

Figure 1:
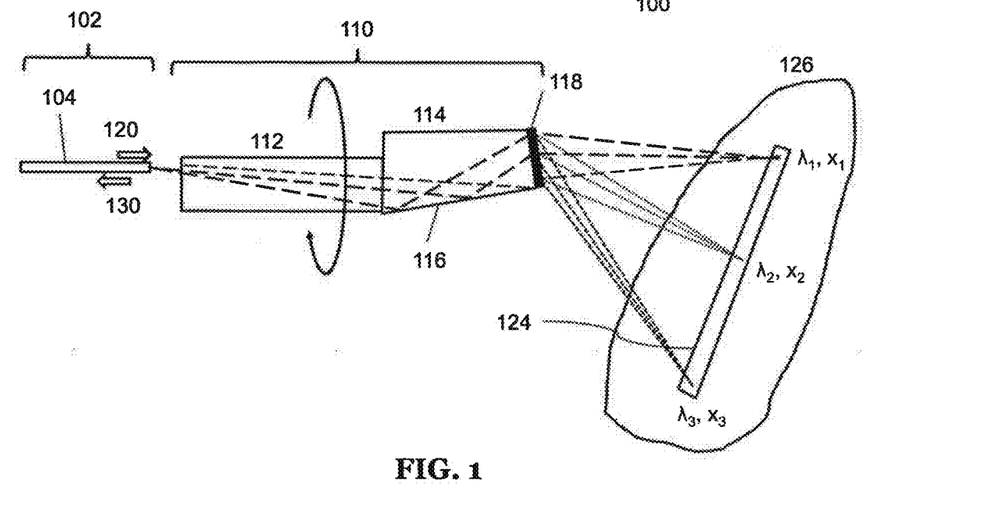
FIG. 1 is a diagram of a probe where only the fiber is fixed.

A diagram of an exemplary embodiment of the SEE probe according to the present disclosure is shown in FIG. 1. The SEE probe 100 includes a light guiding component 102 that includes an optical fiber 104 that is fixed and distal end optics of SEE probe that comprises a rotatable dispersive portion 110 including a focusing component 112 depicted here as a gradient index (GRIN) lens, a spacer 114 having a surface acting as a mirror or other reflector 116, and a dispersive component 118, which may be a grating.

Broadband light (or other electro-magnetic radiation) can be coupled or otherwise provided into the light guiding component 102. The light guiding component 102 is configured to guide the light to the rotatable dispersive portion 110 of the SEE probe. In this embodiment, light from broadband light source comes through the fiber core mode to the lens. The light guiding component 102, which can be or include, for example, a single-mode fiber, a-few-mode fiber, or a multi-mode fiber. The outer diameter of a fiber cladding of the fiber can be, for example 100 µm, 125 µm, or 200 µm, and may be modified if desired. The light is a mixture of various wavelengths that is generally in the visible spectrum, and may also extend into the UV or near IR, as well as into other ranges. The exemplary range of the wavelength can be typically from 400 nm to 800 nm or to 1000 nm. The light (or other electro-magnetic radiation) can be slightly focused after passing though the light focusing component. When the light passes through the probe, it can, for example, propagate in a transparent media against the input wavelength. In some embodiments, the fiber is double clad fiber, the typical core diameter is less than 10 um. The fiber may be used for both illumination 120 and detection 130.

Light from the fixed guiding portion 102 of the SEE probe is directed to the dispersive portion 110 of the probe, where the light is incident on a focusing component 112. The light guiding component 104, shown as an optical fiber, is not attached to the rotatable dispersive portion 110 of the probe so that the rotatable dispersive portion 110 can rotate while the fiber 104 is fixed. The probe has a probe optical axis that is defined as extending along the direction of propagation of a light provided from the light guiding component which is shown here as an optical fiber 104 and through the dispersive component 110. The optical fiber 104 is aligned with the optical axis and this optical axis is the rotation axis of the dispersive component.

The focusing component 112 may be, for example, a GRIN lens which almost collimates but slightly focuses the light. Alternatively, other focusing component(s), such as micro lens(es), can be used instead of a GRIN lens.

The spacer 114 of this embodiment can be, for example, air, glass, or epoxy and is normal-polished at the proximal end, and angle-polished at the distal end shown in FIG. 1. The spacer 114 also includes an angle-polished surface 116 that can be used as mirror when light from the lens 112 is incident on the surface 116. This angle-polished surface 116 can have, for example, a metallic or dielectric coating to increase the reflectivity thereof. The lens 112 can be GRIN lens. The lens 112 is attached to the spacer 114 proximal end. The spacer's distal end, which has been angle-polished, is used as a base for a dispersive element 118 that is shown as a grating. The dimensions of the spacer 114 are determined so that the light coming through the focusing component 112 is reflected by one of the angled surface 116, and goes into the dispersing component 118.

In FIG. 1, the dispersing component 118 is a grating that is located directly on the spacer 114. The grating can have various forms, such as, e.g., standard groove grating, blazed grating, or volume grating including holographic grating and so on. The dispersive component 118 may be a prism. The dispersive component 118 diffracts light into spectrally encoded line 124 which is shown incident on a tissue sample 126.

Each wavelength λ can be focused on a unique spatial location on the target tissue 126 as shown in FIG. 1 as $x_1$, $x_2$, and $x_3$ for wavelengths $\lambda_1$, $\lambda_2$, and $\lambda_3$. Therefore, the light (or other electro-magnetic radiation) can be focused into a spectrally-encoded line 124, rather than onto a point. One of the wavelengths in the light can propagate parallel to the optical axis of the lens, shown as $\lambda_1$ shown in FIG. 1. The location and angle of the optical fiber 104 relative to the lens 112 can be adjusted so that at least one of the wavelengths of the illumination light is substantially parallel to the optical axis of the lens.

Light returned from the target may be detected by the same optics and is thus delivered to a spectrometer through the optical fiber 104. Thus, light (or other electro-magnetic radiation) reflected by the tissue 126 can be coupled or otherwise provided back to the fiber 104, and then can be delivered to a spectrometer (not shown). At the spectrometer, the spectrum of the returning light (or other electro-magnetic radiation) can be read out, which can be used to generate a line image of the tissue using a computer (not shown).

In some embodiments, the optical fiber 104 is a double clad fiber, and the detected light can be delivered through its inner clad mode as well as core mode. In other embodiments, multiple fibers and may be used as the optical fiber 104.

The dispersive portion can be rotated 360° to acquire two-dimensional images of the tissue target from the forward view while the optical fiber 104 is not rotated and so optical fiber rotary junction is not necessary between the fiber and the light source/spectrometer.

In another embodiment (FIG. 2), the configuration is similar to that in the first embodiment in FIG. 1. The spacer 114 and the grating 118 are rotated and the optical fiber 104 is fixed. In this embodiment, the lens 106 is fixed. The lens 106 may be affixed to the optical fiber 104. As shown, the optical fiber 104 is attached at the center of the lens 106 proximal end surface. There may be a space between the lens 106 and the spacer 114. The optical fiber 104 is positioned on the rotation axis of the spacer 114 and grating 118.

Figure 2:
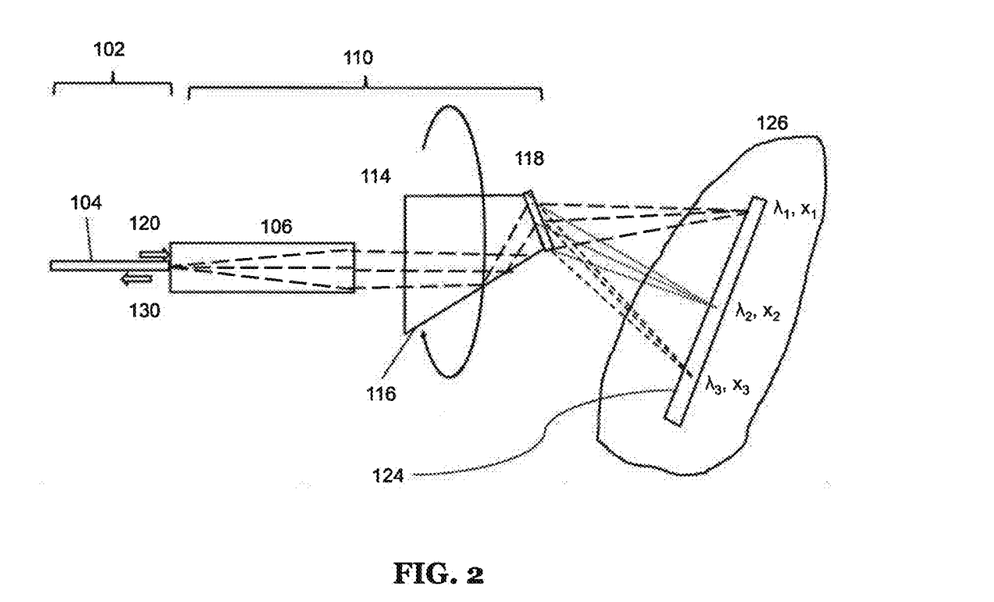
FIG. 2 is a diagram of a probe where the fiber and focusing lens are fixed.

In the embodiments in FIG. 1 and FIG. 2, adjustable focus is realized by changing the gap distance (adjustable space) between the fixed guiding portion 102 and the rotatable dispersive portion 110. This gap distance may be adjusted, for example, during fabrication and then set or it may be configured to be adjustable during use.

In another embodiment (FIG. 3), the configuration is similar to that of the embodiments shown in FIG. 1 and FIG. 2. In this embodiment, instead of a single lens, the lens is divided into two pieces. One such piece is a fixed lens 106 affixed to the optical fiber 104 and the other is a rotating lens 112 that is attached to the spacer 114 proximal end. The lens 106 attached to the fiber 104 collimates the light from the fiber 104 and is a collimating lens. The lens 112 attached to the spacer 114 focuses light slightly (focusing lens).

Figure 3:
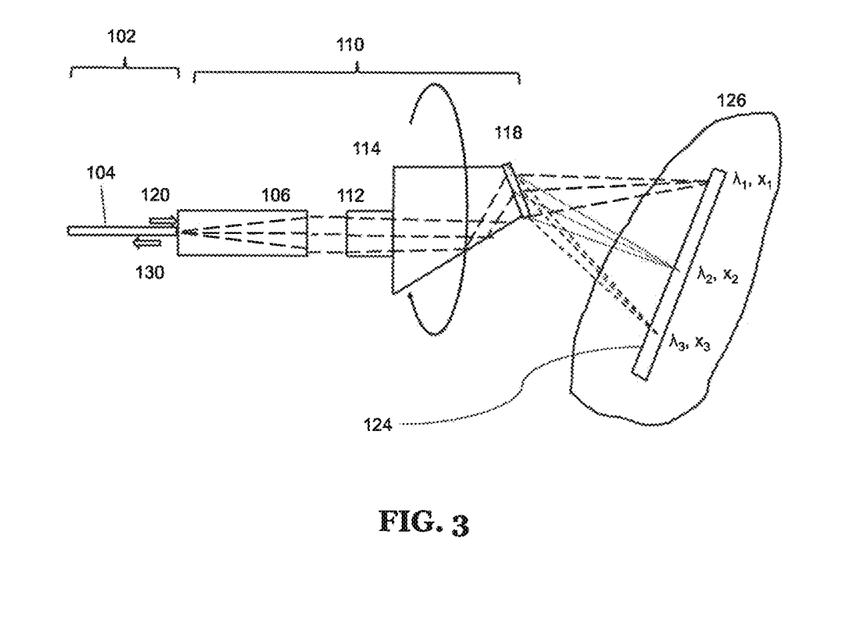
FIG. 3 is a diagram of a probe where the fiber and collimating lens are fixed and the focusing lens is rotated.

The distal end optics forms the rotatable dispersive portion 110 and including the focusing lens pieces 112, spacer 114, and grating 118, is rotated while the fixed guiding portion 102 includes the optical fiber 104 and the collimation lens pieces 112 which are fixed. The fixed guiding portion 102 is positioned to be on the rotation axis of rotatable dispersive portion 110

One of advantage of the embodiment shown in FIG. 3 is that working distance is not changed when the gap distance between the fixed guiding portion 102 and the rotatable dispersive portion 110 is changed, because the light between the collimation lens 106 and focusing lens 112 is collimated. So there will be less problem in imaging even when the gap distance is changed during probe rotation, for example, due to non-uniform rotation distortion. Also that helps improving tolerance of the gap between the static parts and rotating parts in probe fabrication. Thus, there will be less problem in imaging even when the gap distance is changed during probe rotation, for example, due to non-uniform rotation distortion. Also that helps improving tolerance of the gap between the static parts and rotating parts in probe fabrication.

In another embodiment (FIG. 4), hollow core motor 140 and driveshaft 142 can be used to rotate the rotatable dispersive portion 110 shown in the embodiments in FIGS. 1-3.

Figure 4:
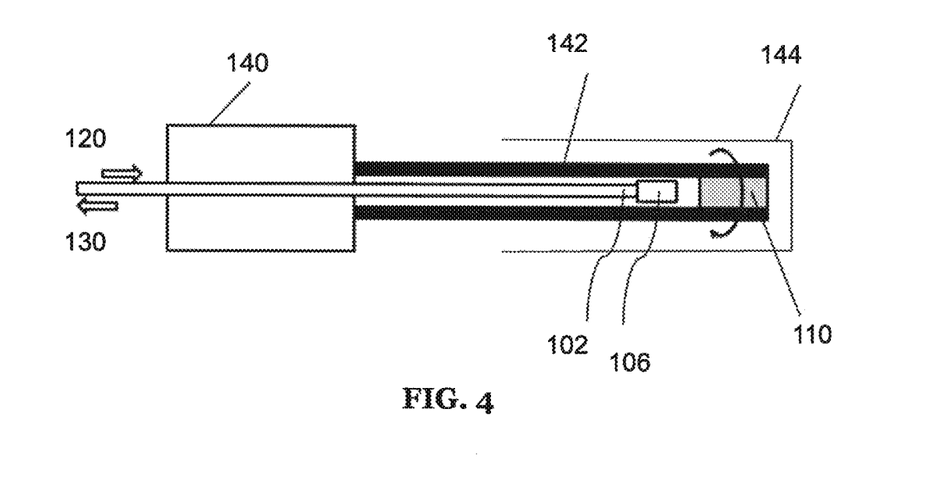
FIG. 4 is a diagram of a hollow core motor and driveshaft for optic rotation.

The rotated distal end optics (rotatable dispersive portion 110) are attached to the tip of the driveshaft 142. The driveshaft 142 delivers the torque from the hollow core motor 140 to the rotatable dispersive portion 110.

The fiber 102 and the lens 106 attached to the fiber 102 are fixed. The fiber 102 can be inside of the hollow core motor 140 where the fiber 102 does not rotate with the hollow core motor 140. An outer sheath 144 covers at least part of the rotatable dispersive portion 110 and the driveshaft 142.

The probe too can be a rigid probe or a flexible probe. In some embodiments, bearings (not shown) can be placed inside of the driveshaft 142. One or more coatings can optionally be added to reduce friction inside the driveshaft 142 and optional bearings.

Figure 5:
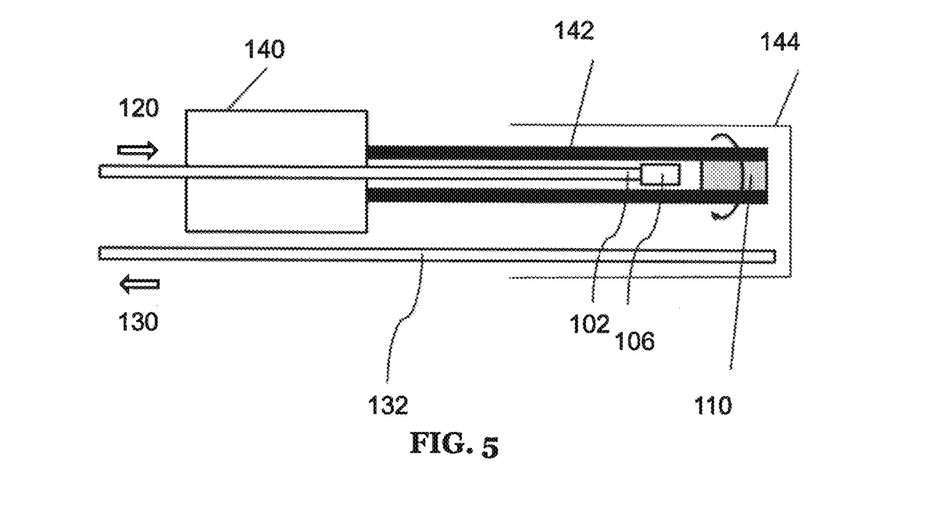
FIG. 5 is a diagram of a hollow core motor where the detection fiber is separated from the illumination fiber.

In other embodiments, the rotating method is not limited to the motor and driveshaft and other means of rotating the rotatable dispersive portion 110 may be used. In other embodiments, instead of a rotary motor, an oscillating In another embodiment (FIG. 5), the detection light path 130 is separated from the illumination light path 120. Light returned from the tissue 126 is detected by detection fiber 132. The detection fiber can be, for example, a multi-mode fiber. In some embodiments, a multi-mode detection fiber having a large core and large NA is preferable to obtain more light returned from the target. For example, the core diameter of the detection fiber 132 can be 100 μm and the NA can be 0.66. In this embodiment, The detection fiber 132 is fixed while the distal end optics of illumination path is rotated. The outer sheath 144 covers illumination distal end optics, the driveshaft 142 and the detection fiber 132. The advantage of having separated path for illumination and detection is that the direct light coupling between illumination and detection path, which causes noise in image, can be decreased.

Figure 6:
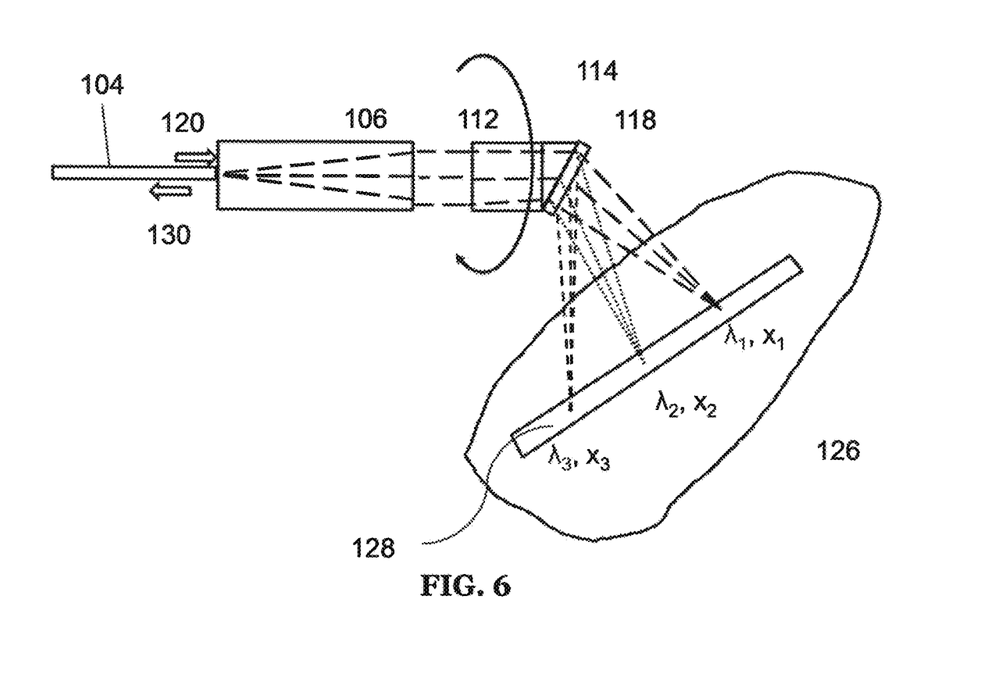
FIG. 6 is a diagram of a probe where the fiber and collimating lens are fixed and the focusing lens is rotated.

In another embodiment (FIG. 6), the fixed fiber scheme can be also used in side view probe where the spectrally encoded line 128 is located in a side-view configuration. In this embodiment, the rotation angle of the distal end optics is not limited to 360 degrees.

In another embodiment (FIG. 7), the detection path is separated from the illumination path. In this embodiment, the detection path includes a fixed detection fiber 132 as well as a rotating detection part 134. The rotation axis of the rotating detection part 134 is different from that of the rotatable dispersive portion 110.

Figure 7:
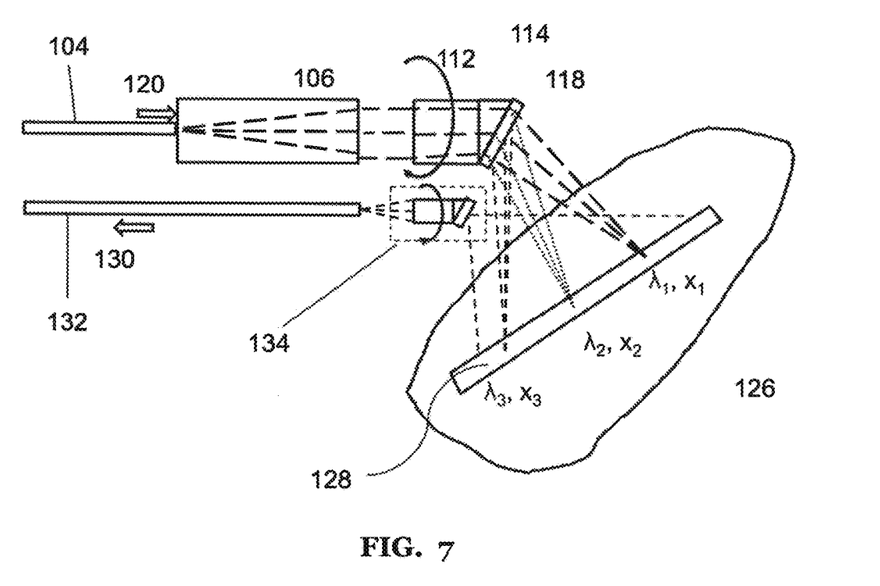
FIG. 7 is a diagram of a probe having two fixed fibers and two rotating gratings.

The rotating detection part 134 can include grating, spacer, and lens.

In another embodiment (FIG. 8), the fixed-fiber scheme can be applied to multiple fiber rotation.

Figure 8:
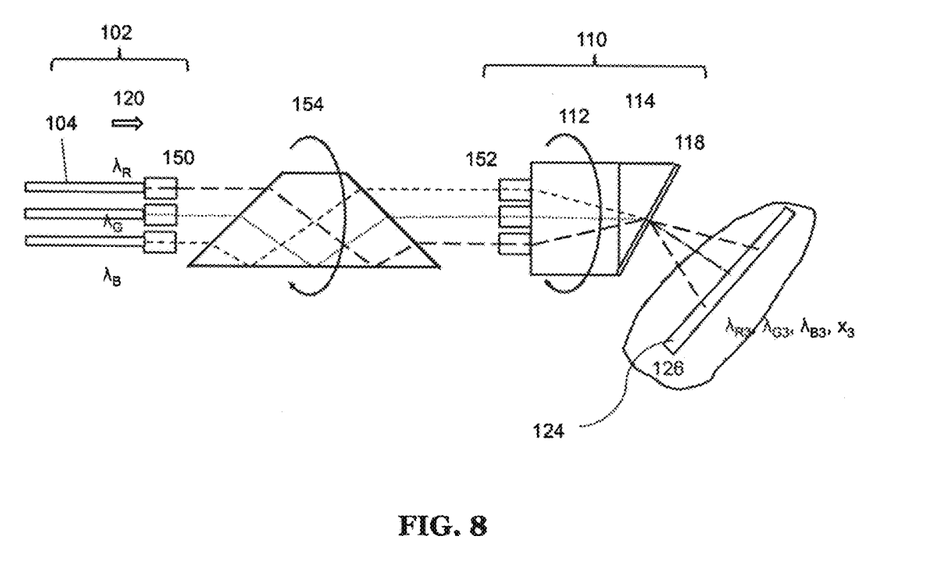
FIG. 8 is a diagram of a probe having two different rotation speeds.

The fixed part can include 3 sets of illumination fibers 104 and collimation lens 150. The rotatable dispersive portion 110 rotating part can be distal end optics which includes grating 118, spacer 114, common lens 112, and 3 small lenses 152, and a dove prism 154. The dove prism 154 is located between the fixed guiding portion 102 and the rotatable dispersive portion 110. The dove prism 154 rotates at half speed of the rotatable dispersive portion 110 so that collimated light from the 3 collimation lens 150 comes into the 3 small lenses 152. The rotation axis of the dove prism 154 is the same as that of the rotatable dispersive portion 110.

The 3 small lens 152 are focusing lenses, and they focus the light on the surface of the common lens 112. The common lens 112 almost collimates but slightly focuses the 3 light. Since the location of the 3 small lens 152 are different, the 3 light are going to the grating 118 with different incident angles. In this exemplary example, The 3 light guiding components 104 are optical fibers delivering bands of light. For example, the bands fall within the red (wavelength: 585-660 nm), green (500-575 nm), and blue (415-490 nm) spectral bands.

The focusing lenses and the small lenses are located so that the spectrally-encoded lines (red, green, and blue) generated by the grating are overlapped. For example, the area of the light beams on the tissue surface may overlap by at least 30%, at least 20%, or at least 10%, or at least 5%.

Two-dimensional color (RGB) image can be obtained by detecting light from the target tissue and scanning the optics. In some embodiments, only two small focusing lens 150 and two small collimating lens 154 may be used. In other embodiments, four small focusing lens 150 and four small collimating lens 154 may be used. In other embodiments the colors chosen for the illumination bands may be selected to maximize contrast in the in vivo environment.

In some embodiments, also described with reference to FIG. 8, a mechanical transmission can be used to achieve two different rotational speeds in the same direction around the same axis of rotation, such that only one rotational input can be used to drive both the dove prism 154 and the rotatable dispersive portion 110. This mechanical transmission could, for example, consist of four to six gears that transmit torque from a cylindrical housing that encases the dove prism 154 to a cylindrical housing that encases the rotatable dispersion portion 110.

Figure 9A:
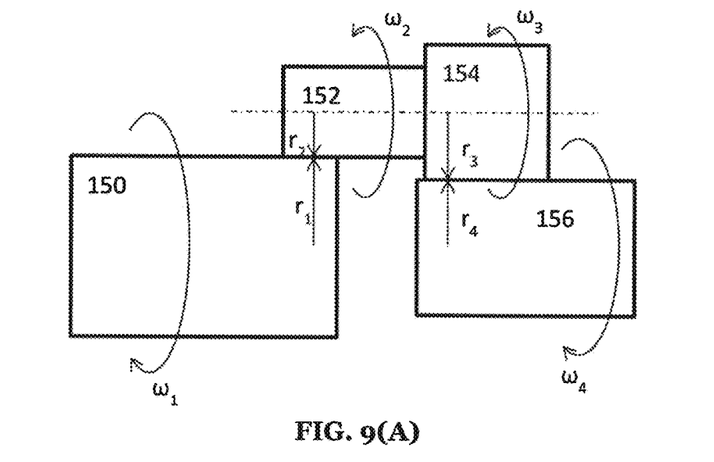
FIGS. 9(A) and 9(B) are examples of mechanical transmission with gears for a first exemplary embodiment (FIG. 9(A) and a second exemplary embodiment (FIG. 9(B)).
Figure 9B:
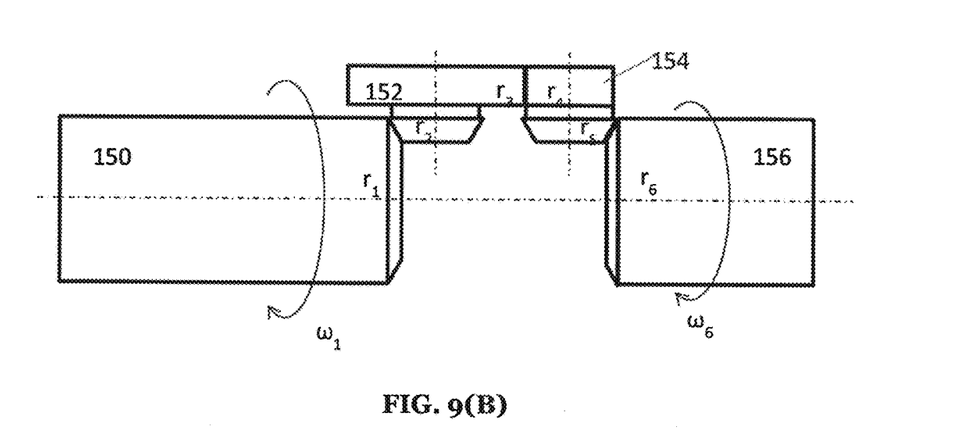

As exemplified in FIGS. 9(A) and 9(B), potential mechanical transmissions are provided where the gear attached to cylindrical housing for dove lens 150 is attached to the gear attached to cylindrical housing for rotatable dispersion portion 156 through two intermediate gears (152 and 154). Each of the gears (150, 152, 154, and 156) in FIG. 9(A) has a radius r ($r_1$, $r_2$, $r_3$ and $r_4$) and an angular velocity $\omega$ ($\omega_1$, $\omega_2$, $\omega_3$ and $\omega_4$), respectively with the gear equations and an exemplary gear ratio that will achieve $\omega_1 = \frac{1}{2}\omega_4$:

| Gear Equations | Gear Ratios (to achieve $\omega_1 = \frac{1}{2} \omega_4$) |
|---|---|
| $r_1\omega_1 = r_2\omega_2$ | |
| $r_3\omega_3 = r_4\omega_4$ | $r_2 = \frac{1}{2} r_1$ |
| $\omega_2 = \omega_3$ | $r_3 = \frac{3}{4} r_1$ |
| $r_1 + r_2 = r_3 + r_4$ | $r_4 = \frac{3}{4} r_1$ |

Similarly, for FIG. 9(B), each of the gears (150, 152, 154, and 156) has a radius r and an angular velocity $\omega$, where intermediate gear 152 has a first radius $r_2$ and first angular velocity $\omega_2$ as well as a second radius $r_3$ and a second angular velocity $\omega_3$. Intermediate gear 154 similarly has a first radius $r_4$ and first angular velocity $\omega_4$ as well as a second radius $r_5$ and a second angular velocity $\omega_5$. The gear attached to cylindrical housing for rotatable dispersion portion 156 has a radius $r_6$ and an angular velocity $\omega_6$. The gear equations and an exemplary gear ratio that will achieve $\omega_1 = \frac{1}{2}\omega_6$ are:

| Gear Equations | Gear Ratios (to achieve $\omega_1 = \frac{1}{2} \omega_6$) |
|---|---|
| $r_1\omega_1 = r_2\omega_2$ | |
| $\omega_2 = \omega_3$ | $r_2 = r_4 = r_5 = \frac{1}{2} r_1$ |
| $r_3\omega_3 = r_4\omega_4$ | $r_1 = r_3 = r_6$ |
| $\omega_4 = \omega_5$ | |
| $r_5\omega_5 = r_6\omega_6$ | |

Figure 10:
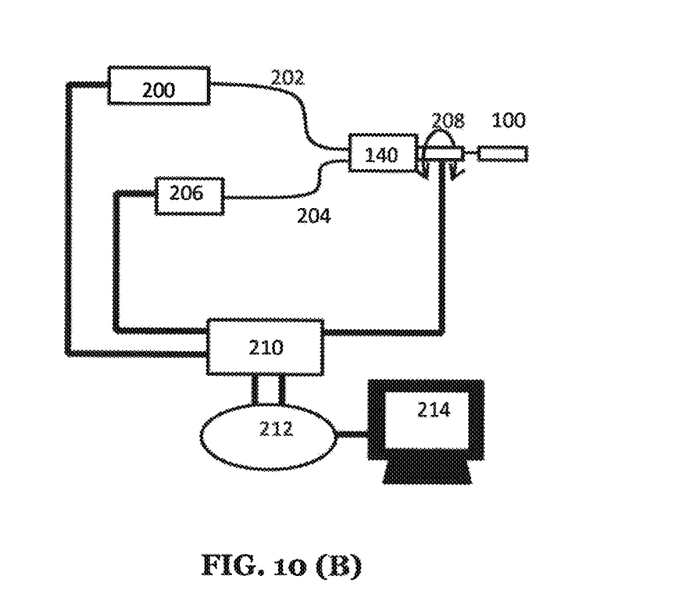
FIGS. 10(A) and 10(B) are diagrams of a system using the probe according to an exemplary embodiment of the present disclosure.
Figure 10A:
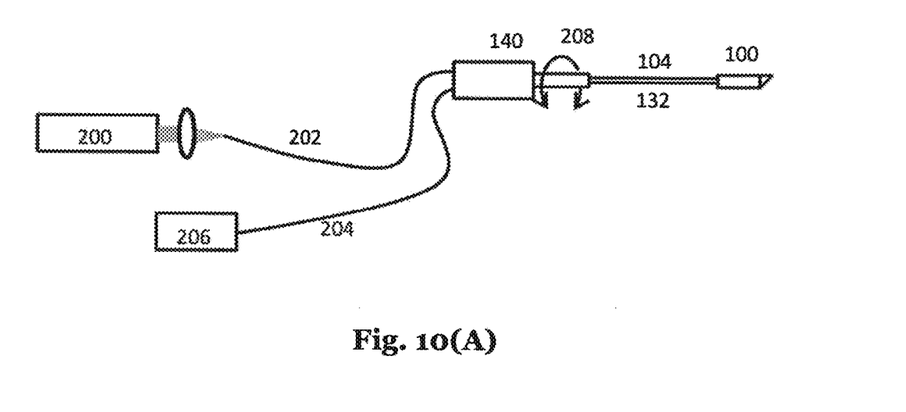

A system to acquire the image from the SEE probe according to an exemplary embodiment of the present disclosure is shown in a diagram of FIG. 10(A). For example, a light source 200 outputs light of broadband spectrum (or other electro-magnetic radiation). The range of the wavelength can be within the visible region, which is from 400 nm thorough 800 nm. However, other wavelengths may also be used. In the exemplary imaging system, the light can be directly guided or otherwise provided into a light guiding component 202, which can be an illumination fiber. The illumination fiber 202 can pass through a hollow core motor 140, after which the exemplary probe 100 is attached. The light scattered back from the object (e.g., tissue) can be collected by a detection fiber 204. The detection fiber 204 can be connected to a detector 206 in which the intensity of selected wavelength can be detected. This exemplary function can be performed by, e.g., a spectrometer.

FIG. 10(B) shows a diagram the imaging system according to another exemplary embodiment of the present disclosure. This exemplary imaging system can be used with, for example, the exemplary probes as described in various exemplary embodiments herein. To operate the exemplary imaging system of FIG. 10(B), a user (e.g., a doctor, nurse, or technician) can connect the exemplary SEE probe 100 having a fixed guiding portion and a rotatable dispersive portion connected to a hollow core motor 140. A computer unit/arrangement 210 can be connected to the light source 200 and to the detector 206. It may also be connected to the hollow core motor 140 (connection not shown).

A command can be transmitted to the computer unit/arrangement 210 via a user interface unit/arrangement 212. A touch panel screen can be includes as part of the user interface unit/arrangement 212, but key board, mouse, joystick, ball controller, and foot pedal can also be included with the user interface unit/arrangement 212. The user can cause a command to be initiated to observe inside the human body through the exemplary SEE probe using the user interface unit 212. For example, when the user inputs a command, the command is transmitted to the central processing unit for execution thereby.

The computer unit/arrangement 210 can include a central processing unit (CPU), memory, input/output interface, detector interface, and/or data storage/RAM. In the data storage, software which configures the central processing unit to perform the determinations and various functions for the user to operate the imaging system can be pre-installed. computer unit/arrangement 210 may comprises other devices as well. The CPU is configured to read and perform computer-executable instructions stored in the Storage/RAM. The computer-executable instructions may include those for the performance of the methods and/or calculations described herein. For example, CPU calculates positional information based on the spectral information from the probe. Storage/RAM includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM may store computer-readable data and/or computer-executable instructions. The components of the computer unit/arrangement may communicate via a bus. The I/O interface provides communication interfaces to input and output devices, which may include a display 214, and/or other devices including a keyboard, a mouse, a printing device, a touch screen, a light pen, an optical storage device, a scanner, a microphone, a camera, a drive, communication cable and a network (either wired or wireless). The detector interface may also provide communication interfaces to input and output devices, which may include photomultiplier tube (PMT), an avalanche photodiode detector (APD). Also, the function of detector may be realized by computer executable instructions (e.g., one or more programs) recorded on a Storage/RAM.

The computer unit/arrangement 210 can be programmed to apply exemplary image processing such as noise reduction, coordinate distortion correction, contrast enhancement and so on. After or even during the image processing is performed, the data can be transmitted from the computer unit/arrangement 210 to a display 214. In some exemplary embodiments, a liquid crystal display can be the display 214. The display 214 can display, for example, the image obtained by the line scan according to various exemplary embodiments of the present disclosure. The display 214 can also display other information than the image, such as the date of observation, what part of the human body is observed, the patient's name, operator's name and so on.

According to certain exemplary embodiments of the use of the SEE probe as described herein, the computer unit/arrangement 210 can then transmit another command to the hollow core motor 140. With this command, the hollow core motor 140 is caused by the computer unit/arrangement 210 to rotate the rotatable dispersive portion of the SEE probe by predetermined amount δθ around the reference axis. After the rotation, the line scan can be considered to be completed, the image data can be sent to the display 214, to be displayed (i.e., with the information regarding the rotation by δθ). Repeating this step can provide a two-dimensional image.

The detector interface also provides communication interfaces to input and output devices, which may include photomultiplier tube (PMT), an avalanche photodiode detector (APD). Also, the function of detector may be realized by computer executable instructions (e.g., one or more programs) recorded on a Storage/RAM.

In an exemplary operation, the user can placed the exemplary SEE probe into a sheath, and then can insert such arrangement/configuration into a predetermined position of a human body. The sheath alone may be inserted into the human body in advance, and it is possible to insert the SEE probe into the sheath after sheath insertion. The exemplary probe can be used to observe inside human body and works as endoscope such as arthroscopy, bronchoscope, sinuscope, vascular endoscope and so on.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

As used herein, the term substantially, such as light propagating substantially parallel or, for example, light having substantially similar angles, means that the difference in angle is less than 15°, or more particularly less than 10°, or more particularly less than 5°, or more particularly less than 3°, or more particularly less than 2°, or more particularly less than 1°.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems, and for example with those described in U.S. Pat. Nos. 7,843,572, 8,145,018, 6,341,036, 7,796,270 and U.S. Patent Application Nos. 2008/0013960 and 2011/0237892, the disclosures of which are incorporated by reference herein in their entireties.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A forward viewing probe having a proximal end and a distal end, comprising:
    a fixed guiding portion and a rotatable dispersive portion arranged in this order from the proximal end to the distal end along a probe optical axis,
    the fixed guiding portion comprising at least a first light guiding component and configured to guide light from a light source to the rotatable dispersive portion, and
    the rotatable dispersive portion comprising at least a reflecting component and a dispersing component,
    wherein at least one of the fixed guiding portion and the rotatable dispersive portion comprises a focusing component,
    wherein the reflecting component is configured to reflect light received from the focusing component towards the dispersing component,
    wherein the dispersing component is configured to receive light from the reflecting component and forward spectrally dispersed light thereof,
    wherein the rotatable dispersive portion is configured to rotate around the probe optical axis, while the fixed guiding portion remains stationary relative to the probe optical axis, and
    wherein the probe is configured such that at least one wavelength of the spectrally dispersed light propagates from the dispersing component substantially parallel to the probe optical axis.

2. The probe of claim 1, wherein the fixed guiding portion comprises a first focusing component.

3. The probe of claim 2, wherein the rotatable dispersive portion comprises a second focusing component.

4. The probe of claim 1, wherein the rotatable dispersive portion is configured to rotate at least 360 degrees in one direction around the probe optical axis.

5. The probe of claim 1, wherein the rotatable dispersive portion is configured to rotate in an oscillating manner around the probe optical axis.

6. The probe of claim 1, wherein the focusing component is a gradient index (GRIN) lens.

7. The probe of claim 1, wherein the rotatable dispersive portion further comprises a spacer component, wherein the reflecting component is located at one surface of the spacer component.

8. The probe of claim 1, wherein the first light guiding component is a single mode optical fiber.

9. The probe of claim 1, wherein the first light guiding component is a multimode optical fiber having a core diameter of less than 50 µm.

10. The probe of claim 1, wherein the first light guiding component is configured to guide illumination light from the light source to the rotatable dispersive portion and to guide detection light collected by the rotatable dispersive portion.

11. The probe of claim 1, further comprising a second light guiding component configured for collecting light associated with the spectrally dispersed light, wherein the second light guiding component is arranged substantially parallel to the first light guiding component.

12. The probe according to claim 1, wherein the first light guiding component is optically connected to the light focusing component at an off-center position.

13. The probe according to claim 1, wherein the at least one wavelength of the spectrally dispersed light has an angle of less than 5° from the probe optical axis.

14. The probe of claim 1, further comprising a rotatable prism located between the fixed guiding portion and the rotatable dispersive portion.

15. The probe of claim 14, wherein the rotatable prism is configured to rotate at approximately half the speed at which the rotatable dispersive portion is configured to rotate.

16. The probe of claim 14, wherein the rotatable prism is a rotatable dove prism.

17. The probe of claim 1, further comprising an adjustable space between the fixed guiding portion and the rotatable dispersive portion.

18. An endoscopic probe having a proximal and a distal end, comprising:
    a fixed guiding portion and a rotatable dispersive portion arranged in this order from the proximal end to the distal end along a probe optical axis,
    the fixed guiding portion comprising a first light guiding component and a first focusing component, and
    the rotatable dispersive portion comprising: a second focusing component and a dispersing component,
    wherein the first focusing component is configured to collimate a light and guide the collimated light to the rotatable dispersive portion,
    wherein the second focusing component is configured to receive the collimated light and forward the collimated light to the dispersing component,
    wherein the dispersing component is configured to receive the light and forward spectrally dispersed light thereof,
    wherein the rotatable dispersive portion is configured to rotate around the probe optical axis, while the fixed guiding portion remains stationary relative to the probe optical axis, and
    wherein the probe is configured such that at least one wavelength of the spectrally dispersed light propagates from the dispersing component substantially parallel to the probe optical axis.

19. The probe of claim 18, further comprising an adjustable space between the fixed guiding portion and the rotatable dispersive portion,
    wherein the adjustable space is an adjustable gap distance between the first focusing component and the second focusing component.

20. An imaging apparatus comprising:
the probe of claim 1,
a light source providing a broad band light to the probe, and
a light intensity detector receiving a light from the probe.

21. The imaging apparatus of claim 20, further comprising a hollow core motor, wherein the rotatable dispersive portion is rotationally attached to a driveshaft of the hollow core motor.

22. The imaging apparatus of claim 20, further comprising a sheath surrounding both the rotatable dispersive portion and the fixed guiding portion.

23. The probe of claim 3, further comprising an adjustable space between the fixed guiding portion and the rotatable dispersive portion,
   wherein the first focusing component is a collimating lens and the second focusing component is a focusing lens,
   wherein the adjustable space is an adjustable gap distance between the collimating lens and the focusing lens, and
   wherein a working distance of the probe is not changed when the gap distance is changed.

* * * * *